(12) United States Patent
Salce, Jr. et al.

(10) Patent No.: US 9,592,215 B2
(45) Date of Patent: Mar. 14, 2017

(54) TOPICAL ANALGESIC LOTION

(71) Applicant: SYNERGISTIC THERAPEUTICS, LLC, Naples, FL (US)

(72) Inventors: Anthony H. Salce, Jr., Naples, FL (US); William F. Greenwood, Fairfield, CT (US); Shivsankar Misir, Naples, FL (US)

(73) Assignee: Synergistic Therapeutics, LLC, Naples, FL (US)

( * ) Notice: Subject to any disclaimer, the term of this patent is extended or adjusted under 35 U.S.C. 154(b) by 0 days.

(21) Appl. No.: 15/229,434

(22) Filed: Aug. 5, 2016

(65) Prior Publication Data

US 2017/0035715 A1  Feb. 9, 2017

Related U.S. Application Data

(60) Provisional application No. 62/201,264, filed on Aug. 5, 2015.

(51) Int. Cl.
| | | |
|---|---|---|
| *A61K 31/195* | (2006.01) | |
| *A61K 31/135* | (2006.01) | |
| *A61K 31/16* | (2006.01) | |
| *A61K 31/196* | (2006.01) | |
| *A61K 31/197* | (2006.01) | |
| *A61K 31/137* | (2006.01) | |
| *A61K 31/167* | (2006.01) | |
| *A61K 9/00* | (2006.01) | |

(52) U.S. Cl.
CPC .......... *A61K 31/196* (2013.01); *A61K 9/0014* (2013.01); *A61K 31/135* (2013.01); *A61K 31/137* (2013.01); *A61K 31/167* (2013.01); *A61K 31/197* (2013.01)

(58) Field of Classification Search
CPC ..... A61K 31/195; A61K 31/135; A61K 31/16
USPC ................................. 514/561, 647, 649, 626
See application file for complete search history.

(56) References Cited

U.S. PATENT DOCUMENTS

| | | | |
|---|---|---|---|
| 2003/0124176 A1* | 7/2003 | Hsu ....................... | A61K 8/0208 424/449 |
| 2007/0014733 A1* | 1/2007 | O'Donnell ........... | C07D 311/58 424/45 |
| 2007/0292461 A1* | 12/2007 | Tamarkin ................. | A61K 8/86 424/401 |
| 2010/0183519 A1* | 7/2010 | Katz .................... | A61K 9/0014 424/9.2 |

* cited by examiner

*Primary Examiner* — Raymond Henley, III
(74) *Attorney, Agent, or Firm* — Moritt Hock & Hamroff LLP; Steven S. Rubin, Esq.

(57) ABSTRACT

Technologies are described for a formulation and production of a formulation. The methods may comprise depositing a non-steroidal anti-inflammatory drug (NSAID) compound into a chamber. The methods may comprise depositing a muscle relaxant into the chamber. The methods may comprise depositing a calcium channel blocker into the chamber. The methods may comprise depositing a general anesthetic into the chamber. The methods may comprise depositing a local anesthetic into the chamber. The methods may comprise milling and mixing the NSAID compound, the muscle relaxant, the calcium channel blocker, the general anesthetic, and the local anesthetic into a powder. The methods may comprise adding a solvent with the powder. The methods may comprise mixing the solvent with the powder to form a solution. The methods may comprise adding a base cream to the solution. The methods may comprise mixing the base cream and the solution to form the formulation.

19 Claims, 2 Drawing Sheets

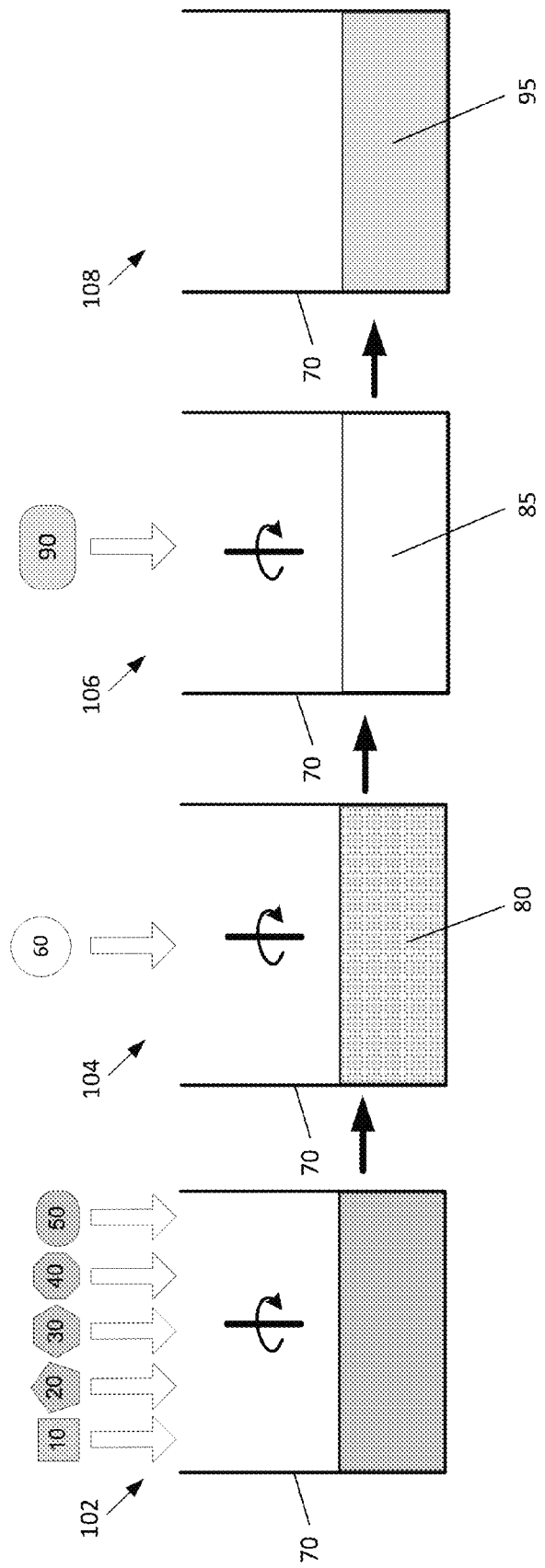

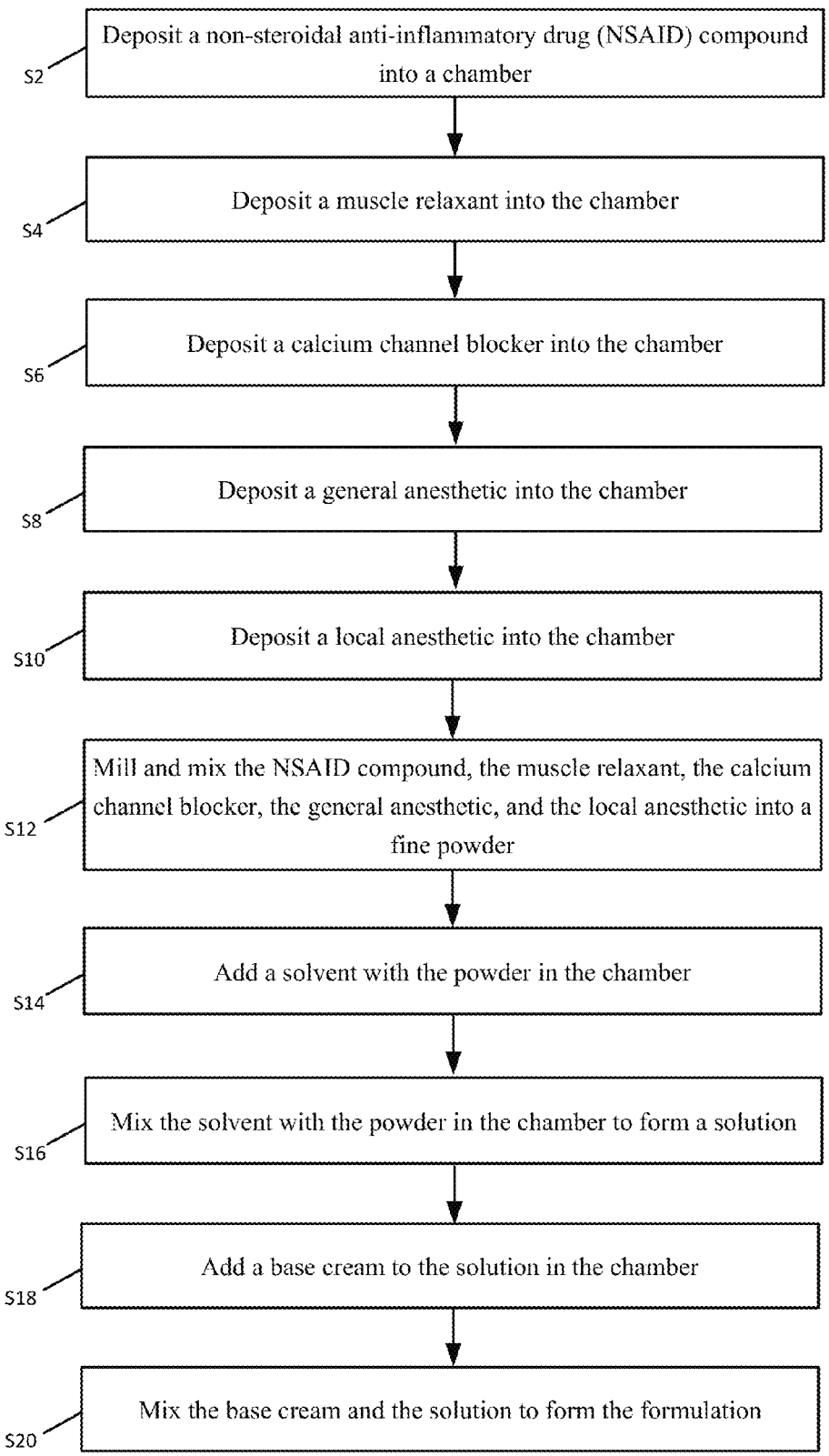

TOPICAL ANALGESIC LOTION

BACKGROUND

Non-steroidal anti-inflammatory drugs (NSAIDs) may reduce substances in the body that cause pain and inflammation. NSAIDs may work by blocking cyclooxygenase enzymes which produce prostaglandins in the cells, reducing inflammation and pain. NSAIDs are typically used to treat pain and arthritis symptoms such as joint inflammation, swelling, stiffness, and pain.

SUMMARY

In some examples formulations are described. The formulations may comprise 5 to 10 weight percent of a non-steroidal anti-inflammatory drug (NSAID). The formulations may comprise 5 to 10 weight percent of a muscle relaxant. The formulations may comprise 0.01 to 0.05 weight percent of a calcium channel blocker. The formulations may comprise 0.005 to 0.010 weight percent of a general anesthetic. The formulations may comprise 2 to 10 weight percent of a local anesthetic.

In some examples, methods to produce a formulation are described. The methods may comprise depositing a non-steroidal anti-inflammatory drug (NSAID) compound into a chamber. The methods may comprise depositing a muscle relaxant into the chamber. The methods may comprise depositing a calcium channel blocker into the chamber. The methods may comprise depositing a general anesthetic into the chamber. The methods may comprise depositing a local anesthetic into the chamber. The methods may comprise milling and mixing the NSAID compound, the muscle relaxant, the calcium channel blocker, the general anesthetic, and the local anesthetic into a powder. The methods may comprise adding a solvent with the powder in the chamber. The methods may comprise mixing the solvent with the powder in the chamber to form a solution. The methods may comprise adding a base cream to the solution in the chamber. The methods may comprise mixing the base cream and the solution to form the formulation.

In some examples, formulations may be described. The formulations may comprise about 5 to about 10 weight percent of a NSAID. The formulations may comprise about 5 to about 10 weight percent of a muscle relaxant. The formulations may comprise about 0.01 to about 0.05 weight percent of a calcium channel blocker. The formulations may comprise about 0.005 to about 0.010 weight percent of a general anesthetic. The formulations may comprise about 2 to about 10 weight percent of a local anesthetic. The formulations may comprise a solvent. The formulations may comprise a base cream.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 illustrates an example system that can be utilized to produce a topical analgesic lotion; and FIG. 2 illustrates a flow diagram of an example process to produce an analgesic topical lotion;

all arranged according to at least some embodiments described herein.

DETAILED DESCRIPTION

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example system that can be utilized to produce a topical analgesic lotion, arranged in accordance with at least some embodiments presented herein. As discussed in more detail below, a topical analgesic lotion may be effective in the treatment pain and inflammation.

System 100 may include a compound 10, a compound 20, a compound 30, a compound 40, a compound 50, a solvent 60, and a chamber 70. Compound 10 may be a non-steroidal anti-inflammatory drug (NSAID). Compound 10 may reduce substances in the body that cause pain and inflammation. Compound 10 may include diclofenac with formula $C_{14}H_{11}Cl_2NO_2$ or a diclofenac diethylammonium salt with formula $C_{18}H_{22}Cl_2N_2O_2$. Compound 10 may be deposited into chamber 70.

Compound 20 may be a muscle relaxant. Compound 20 may treat muscle symptoms such as spasm, pain, and stiffness. Compound 20 may be incorporated as a skeletal muscle relaxant and anti-spastic agent. Compound 20 may be a structural analog of the inhibitory neurotransmitter gamma-aminobutyric acid (GAGA), and may exert its effects by stimulation of $GABA_B$ receptors. Compound 20 may be baclofen with formula $C_{10}H_{12}ClNO_2$. Compound 20 may be deposited into chamber 70.

Compound 30 may be a calcium channel blocker. Compound 30 may be a phenylalkylamine calcium channel blocker and may treat hypertension and cluster headaches. Compound 30 may be an ionic calcium influx inhibitor more commonly known as a calcium channel blocking agent. Compound 30 may inhibit the transmembrane influx of extracellular calcium ions across the membrane of myocardial cells and vascular smooth muscle cells. Compound 30 may be verapamil with formula $C_{27}H_{38}N_2O_4$. Compound 30, by inhibiting calcium influx, may inhibit the contractile processes, and may thereby dilate the main outer layers of the skin to allow penetration of the topical lotion. Compound 30 may be deposited into chamber 70.

Compound 40 may be a general anesthetic. Compound 40 may decrease peripheral nociceptive signaling on peripheral nerves by a non-competitive blockade of N-methyl-D-aspartate receptors in the peripheral nerves. Compound 40 may be ketamine with formula $C_{13}H_{16}ClNO$. Compound 40 may be deposited into chamber 70.

Compound 50 may be a local anesthetic. Compound 50 may block a pathway of pain signals along nerves. Compound 50 may stop sodium entering a nerve ending and prevent an electric signal from building up and passing along nerve fibers to the brain. Compound 50 may reduce pain or discomfort caused by skin irritations. Compound 50 may be lidocaine with formula $C_{14}H_{22}N_2O$ or benzocaine with formula $C_9H_{11}NO_2$. Compound 50 may be deposited into chamber 70.

At 102, compound 10, compound 20, compound 30, compound 40, and compound 50 in chamber 70 may be deposited into chamber 70. Compound 10, compound 20, compound 30, compound 40, and compound 50 may be milled and mixed into a fine powder 80 (as shown at 104). Milling and mixing may be performed either by hand or machine. Powder 80 may include particulates with a particle size from 1 micron to 40 microns.

At 104, a solvent 60 may be added with powder 80 in chamber 70. Solvent 60 may be mixed with powder 80 in chamber 70 until a clear solution 85 is formed (as shown at 106). Solution 85 may include powder 80 dispersed in solvent 60. Mixing may be performed either by hand or machine. Solvent 60 may include propylene glycol, water, alcohol, or mineral oil and combinations thereof.

At 106, a base cream 90 may be added with solution 85 in chamber 70. Base cream 90 may be mixed with solution 85 in chamber 70 to form topical analgesic lotion 95 (as shown at 108). Mixing may be performed either by hand or machine. An amount of base cream 90 may be added in proportion to an amount of solution 85 so as to achieve a desired weight % of compound 10, compound 20, compound 30, compound 40, and compound 50 respectively in topical analgesic lotion 95. Base cream 90 may include a moisturizing skin cream. Base cream 90 may include VANICREAM. Base cream 90 may be selected so that base cream 90 includes properties that allow absorption of base cream 90 through the passageways of skin. Base cream 90 may be selected so that base cream 90 may substantially prevent fluid washout of solution 85 from topical analgesic lotion 95. Base cream 90 may be selected so that base cream 90 may provide stability to topical analgesic lotion 95.

Compound 10 may comprise from 5.0% by weight to 10.0% by weight of topical analgesic lotion 95. Compound 20 may comprise from 5.0% by weight to 10.0% by weight of topical analgesic lotion 95. Compound 30 may comprise from 0.01% by weight to 0.05% by weight of topical analgesic lotion 95. Compound 40 may comprise from 0.005% by weight to 0.010% by weight of topical analgesic lotion 95. Compound 50 may comprise from 2.0% by weight to 10.0% by weight of topical analgesic lotion 95.

FIG. 2 illustrates a flow diagram of an example process to produce a topical analgesic lotion 95. The process in FIG. 2 could be implemented using, for example, system 100 discussed above. An example process may include one or more operations, actions, or functions as illustrated by one or more of blocks S2, S4, S6, S8, S10, S12, S14, S16, S18, and/or S20. Although illustrated as discrete blocks, various blocks may be divided into additional blocks, combined into fewer blocks, or eliminated, depending on the desired implementation.

Processing may begin at block S2, "Deposit a non-steroidal anti-inflammatory drug (NSAID) compound into a chamber." At block S2, a NSAID compound may be deposited into a chamber. The NSAID compound may reduce substances in the body that cause pain and inflammation. The NSAID compound may include diclofenac with formula $C_{14}H_{11}Cl_2NO_2$ or a diclofenac diethylammonium salt with formula $C_{18}H_{22}Cl_2N_2O_2$.

Processing may continue from block S2 to block S4, "Deposit a muscle relaxant into the chamber." At block S4, a muscle relaxant may be deposited into the chamber. The muscle relaxant may be incorporated as a skeletal muscle relaxant and anti-spastic agent. The muscle relaxant may be a structural analog of the inhibitory neurotransmitter gamma-aminobutyric acid (GAGA), and may exert its effects by stimulation of $GABA_B$ receptors. The muscle relaxant may be baclofen with formula $C_{10}H_{12}ClNO_2$.

Processing may continue from block S4 to block S6, "Deposit a calcium channel blocker into the chamber." At block S6, a calcium channel blocker may be deposited into the chamber. The calcium channel blocker may be a phenylalkylamine calcium channel blocker and may treat hypertension and cluster headaches. The calcium channel blocker may be an ionic calcium influx inhibitor more commonly known as a calcium channel blocking agent. The calcium channel blocker may inhibit the transmembrane influx of extracellular calcium ions across the membrane of myocardial cells and vascular smooth muscle cells. The calcium channel blocker may be verapamil with formula $C_{27}H_{38}N_2O_4$.

Processing may continue from block S6 to block S8, "Deposit a general anesthetic into the chamber." At block S8, a general anesthetic may be deposited into the chamber. The general anesthetic may decrease peripheral nociceptive signaling on peripheral nerves by a non-competitive blockade of N-methyl-D-aspartate receptors in the peripheral nerves. The general anesthetic may be ketamine with formula $C_{13}H_{16}ClNO$.

Processing may continue from block S8 to block S10, "Deposit a local anesthetic into the chamber." At block S10, a local anesthetic may be deposited into the chamber. The local anesthetic may block a pathway of pain signals along nerves. The local anesthetic may stop sodium entering a nerve ending and prevent an electric signal from building up and passing along nerve fibers to the brain. The local anesthetic may reduce pain or discomfort caused by skin irritations. The local anesthetic may be lidocaine with formula $C_{14}H_{22}N_2O$ or benzocaine with formula $C_9H_{11}NO_2$.

Processing may continue from block S10 to block S12, "Mill and mix the NSAID compound, the muscle relaxant, the calcium channel blocker, the general anesthetic, and the local anesthetic into a fine powder." At block S12, the NSAID component, the muscle relaxant, the calcium channel blocker, the general anesthetic, and the local anesthetic may be milled and mixed into a fine powder. The milling and mixing may be performed either by hand or machine. The powder may include particulates with a particle size from 1 micron to 40 microns.

Processing may continue from block S12 to block S14, "Add a solvent with the powder in the chamber." At block S14, a solvent may be added to the powder in the chamber. The solvent may include propylene glycol, water, alcohol, or mineral oil and combinations thereof.

Processing may continue from block S14 to block S16, "Mix the solvent with the powder in the chamber to form a solution." At block S16, the solvent may be mixed with the powder in the chamber. The solvent may be mixed with the powder in the chamber until a clear solution is formed with the powder dispersed in the solvent to form a solution. Mixing may be performed either by hand or machine.

Processing may continue from block S16 to block S18, "Add a base cream to the solution in the chamber." At block S18, a base cream may be added to the solution in the chamber. An amount of the base cream may be added in proportion to an amount of the solution in the chamber so as to achieve a desired weight % of NSAID compound, muscle relaxant, calcium channel blocker, general anesthetic, and local anesthetic respectively in the formulation. The base cream may include a moisturizing skin cream. The base cream may include VANICREAM. The base cream may substantially allow absorption of the base cream through the passageways of skin. The base cream may substantially prevent fluid washout of the solution in the formulation. The base cream may provide stability to the formulation.

Processing may continue from block S18 to block S20, "Mix the base cream and the solution to form the formulation." At block S10, the base cream may be mixed with the solution to form the formulation.

A system in accordance with the present disclosure may be an effective topical treatment for pain. An embodiment of the present application may be highly stable and provide high skin penetration. An embodiment of the present application may provide a rapid achievement of NSAID concentration in a user's blood. A system in accordance with the present disclosure may provide treatment without irritation. An embodiment of the present application may be effective for the treatment of pain with complete dissolution of the active NSAID. In some cases, a topical analgesic may be preferred over another treatment form, such as an oral pill.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A formulation comprising:
   5 to 10 weight percent of a non-steroidal anti-inflammatory drug (NSAID);
   5 to 10 weight percent of a muscle relaxant;
   0.01 to 0.05 weight percent of a calcium channel blocker;
   0.005 to 0.010 weight percent of a general anesthetic; and
   2 to 10 weight percent of a local anesthetic.

2. The formulation of claim 1, wherein the NSAID includes diclofenac and has a formula of $C_{14}H_{11}Cl_2NO_2$ or a diclofenac diethylammonium salt with a formula of $C_{18}H_{22}Cl_2N_2O_2$.

3. The formulation of claim 1, wherein the muscle relaxant includes baclofen with a formula of $C_{10}H_{12}ClNO_2$.

4. The formulation of claim 1, wherein the calcium channel blocker includes verapamil with a formula of $C_{27}H_{38}N_2O_4$.

5. The formulation of claim 1, wherein the general anesthetic includes ketamine with a formula of $C_{13}H_{16}ClNO$.

6. The formulation of claim 1, wherein the local anesthetic includes lidocaine with a formula of $C_{14}H_{22}N_2O$ or benzocaine with a formula of $C_9H_{11}NO_2$.

7. The formulation of claim 1, further comprising a solvent.

8. The formulation of claim 7, wherein the solvent includes propylene glycol, water, alcohol, mineral oil, or combinations thereof.

9. The formulation of claim 1, wherein:
   the NSAID includes diclofenac;
   the muscle relaxant includes baclofen;
   the calcium channel blocker includes verapamil;
   the general anesthetic includes ketamine; and
   the local anesthetic includes lidocaine.

10. A method to produce a formulation, the method comprising:
    depositing a non-steroidal anti-inflammatory drug (NSAID) compound into a chamber;
    depositing a muscle relaxant into the chamber;
    depositing a calcium channel blocker into the chamber;
    depositing a general anesthetic into the chamber;
    depositing a local anesthetic into the chamber;
    milling and mixing the NSAID compound, the muscle relaxant, the calcium channel blocker, the general anesthetic, and the local anesthetic into a powder;
    adding a solvent with the powder in the chamber;
    mixing the solvent with the powder in the chamber to form a solution;
    adding a base cream to the solution in the chamber; and
    mixing the base cream and the solution to form the formulation.

11. The method of claim 10, wherein the NSAID includes diclofenac.

12. The method of claim 10, wherein the muscle relaxant includes baclofen.

13. The method of claim 10, wherein the calcium channel blocker includes verapamil.

14. The method of claim 10, wherein the general anesthetic includes ketamine.

15. The method of claim 10, wherein the local anesthetic includes lidocaine.

16. The method of claim 10, wherein the solvent includes propylene glycol, water, alcohol, mineral oil, or combinations thereof.

17. The method of claim 10, wherein:
    the NSAID includes diclofenac;
    muscle relaxant includes baclofen;
    the calcium channel blocker includes verapamil;
    the general anesthetic includes ketamine; and
    the local anesthetic includes lidocaine.

18. A formulation comprising:
    about 5 to about 10 weight percent of a NSAID;
    about 5 to about 10 weight percent of a muscle relaxant;
    about 0.01 to about 0.05 weight percent of a calcium channel blocker;
    about 0.005 to about 0.010 weight percent of a general anesthetic;
    about 2 to about 10 weight percent of a local anesthetic;
    a solvent; and
    a base cream.

19. The formulation of claim 18, wherein:
    the NSAID includes diclofenac;
    muscle relaxant includes baclofen;
    the calcium channel blocker includes verapamil;
    the general anesthetic includes ketamine;
    the local anesthetic includes lidocaine; and
    the solvent includes propylene glycol, water, alcohol, mineral oil, or combinations thereof.

* * * * *